United States Patent
Bergmann et al.

(10) Patent No.: US 9,217,742 B2
(45) Date of Patent: *Dec. 22, 2015

(54) METHOD FOR RISK STRATIFICATION IN STABLE CORONARY ARTERY DISEASE

(71) Applicant: B.R.A.H.M.S GmbH, Hennigsdorf (DE)

(72) Inventors: Andreas Bergmann, Berlin (DE); Joachim Struck, Berlin (DE); Nils G. Morgenthaler, Berlin (DE); Jana Papassotiriou, Berlin (DE); Stefan Blankenberg, Frankfurt (DE); Karl Lackner, Mainz (DE); Hans Rupprecht, Mainz (DE); Christoph Bickel, Koblenz (DE)

(73) Assignee: B.R.A.H.M.S. GmbH, Hennigsdorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/223,517

(22) Filed: Mar. 24, 2014

(65) Prior Publication Data

US 2015/0087727 A1  Mar. 26, 2015

Related U.S. Application Data

(63) Continuation of application No. 12/671,823, filed as application No. PCT/EP2008/006378 on Aug. 1, 2008, now Pat. No. 8,735,079.

(30) Foreign Application Priority Data

Aug. 3, 2007  (EP) .................................. 07015271

(51) Int. Cl.
*G01N 33/53* (2006.01)
*G01N 33/74* (2006.01)

(52) U.S. Cl.
CPC ................ *G01N 33/53* (2013.01); *G01N 33/74* (2013.01); *G01N 2333/585* (2013.01); *G01N 2800/323* (2013.01); *G01N 2800/324* (2013.01); *G01N 2800/54* (2013.01)

(58) Field of Classification Search
None
See application file for complete search history.

(56) References Cited

U.S. PATENT DOCUMENTS

2012/0122233 A1  5/2012  Bergmann et al.

OTHER PUBLICATIONS

Assicot et al., "High serum procalcitonin concentrations in patients with sepsis and infection", The Lancet, vol. 341, No. 8844; Feb. 27, 1993, 515-518.
Blankenberg et al., "Glutathione Peroxidase 1 Activity and Cardiovascular Events in Patients with Coronary Artery Disease", The New England Journal of Medicine, vol. 349(17); Oct. 23, 2003, 1605-1613.
Bugden et al., "The potential role of procalcitonin in the emergency department management of febrile young adults during a sustained meningococcal epidemic", Emergency Medicine Australasia, vol. 16; 2004. 114-119.
Chiwakata et al., "Procalcitonin as a Parameter of Disease Severity and Risk of Mortality in Patients with *Plasmodium falciparum* Malaria", The Journal of Infectious Diseases, vol. 183; 2001, 1161-4.
Christ-Crain et al., "Procalcitonin Guidance of Antibiotic Therapy in community-acquired Pneumonia", Am | Respir Crit Care Med, vol. 174; 2006, 84-93.
Christ-Crain et al., "Effect of procalcitonin-guided treatment on antibiotic use and outcome in lower respiratory tract infections: cluster-randomised, single-blinded intervention trial", Lancet, vol. 363; 2004, 600-07.
Clec'h et al., "Diagnostic and prognostic value of procalcitonin in patients with septic shock", Critical Care Medicine, vol. 32, No. 5; 2004, 1166-1169.
De Werra et al., "Cytokines, nitrite/nitrate, soluble tumor necrosis factor receptors, and procalcitonin concentrations: Comparisons in patients with septic shock, cardiogenic shock, and bacterial pneumonia", Crit Care Med, vol. 25, No. 4; 1997, 607-613.
Erren et al., "Systemic Inflammatory Parameters in Patients With Atherosclerosis of the Coronary and Peripheral Arteries", Arterioscler Thromb Vasc Biol., vol. 19; 1999, 2355-2363, XP002346643 ISSN: 1079-5642.
Ferriere et al., "Procalcitonin in Unstable Coronary Artery Disease, Relation to Chlamydia, Pneumoniae Serology", Clin Chem lab Med, vol. 37 Special Supplement; 1999; S445, Abstract H076, International Federation of clinical and Laboratory Medicine (17$^{th}$ International and 1; Florence, Italy; Jun. 6-11, 1999 issn: 1434-6621.
Hoffman et al., "Procalcitonin amplifies inducible nitric oxide synthase gene expression and nitric oxide production in vascular smooth muscle cells", Crit Care Med, vol. 30, No. 9; 2002, 2091-2095.
Ilhan et al., "Procalcitonin, c-reactive protein and neopterin levels in patients with coronary atherosclerosis", Acta Cardiologica, vol. 60, No. 4; 2005, 361-365.
Lee et al., "Predictive Comparisons of Procalcitonin (PCT) Level, Arterial Ketone Body Ratio (AKBR), APACHE III Score and Multiple Organ Dysfunction Score (MODS) in Systemic Inflammatory Response Syndrome (SIRS)", Yonsei Medical Journal, vol. 45 No. 1; 2004, 29-37.
Linscheid et al., "Expression and secretion of procalcitonin and calcitonin gene-related peptide by adherent monocytes and by macrophage-activated adipocytes", Crit Care Med, vol. 32, No. 8; 2004, 1715-1721.

(Continued)

*Primary Examiner* — Jacob Cheu
(74) *Attorney, Agent, or Firm* — Heslin Rothenberg Farley and Mesiti, PC

(57) ABSTRACT

An in vitro method for the risk stratification of patients with stable arteriosclerosis, especially stable coronary artery disease, is disclosed wherein the concentration of procalcitonin is determined in the circulation of such patients using a highly sensitive PCT assay, and wherein within the range of PCT concentrations in the typical normal range of healthy individuals cutoff values are defined which distinguish groups of individual patients with stable arteriosclerosis in accordance with personal cardiac risk, and patients are allotted to one of said risk groups on the basis of their individual PCT concentrations.

2 Claims, 3 Drawing Sheets

(56) References Cited

OTHER PUBLICATIONS

Mackay et al., "Tumor Necrosis Factor α (TNF- α)-induced Cell Adhesion to Human Endothelial Cells is under Dominant Control of One TNF Receptor Type, TNF-R55", J. Exp. Med., vol. 177; 1993, 1277-1286.

Meisner, "Biomarkers of sepsis: clinically useful?", Current Opinion in Critical Care, vol. 11; 2005, 473-480.

Meisner et al., "Correlation of procalcitonin and c-reactive protein to inflammation, complications, and outcome during the intensive care unit course of multiple-trauma patients", Critical Care, vol. 10, No. 1; 2006.

Meisner et al., "Early increase of procalcitonin after cardiovascular surgery in patients with postoperative complications", Intensive Care Med, vol. 28; 2002, 1094-1102.

Meisner et al., "Postoperative plasma concentrations of procalcitonin after different types of surgery", Intensive Care Med, vol. 24; 1998, 680-684.

Morgenthaler et al., "Sensitive Immunoluminometric Assay for the Detection of Procalcitonin", Clinical Chemistry, vol. 48, No. 5; 2002, 788-790.

Mueller, C., "The Use of B-Type Natriuretic Peptides in Coronary Artery Disease: Utile or Futile?", Journal of American College of Cardiology, vol. 50, No. 3; 2007, 215-216.

Oberhoffer et al., "Outcome Prediction by Traditional and New Markers of Inflammation in Patients with Sepsis", Clin Chem lab Med. vol. 37, No. 3; 1999, 363-368.

Oberhoffer et al., "Procalcitonin expression in human peripheral blood mononuclear cells and its modulation by lipopolysaccharides and sepsis-related cytokines in vitro", J Lab Clin Med, vol. 134; 1999, 49-55.

Omland et al., "B-Type Natriuretic Peptide and Long-Term Survival in Patients With Stable Coronary Artery Disease", The American Journal of Cardiology, vol. 95; 2005, 24-28.

Omland et al., "Prognostic Value of B-Type Natriuretic Peptides in Patients With Stable Coronary Artery Disease: The PEACE Trial", Journal of the American College of Cardiology, vol. 50, No. 3; 2007, 205-214.

Pischon et al., "Non-High-Density Lipoprotein Cholesterol and Apoliprotein B in the Prediction of Coronary Heart Disease in Men", Circulation 112: 3375-3383, 2005.

Polk et al., "B-type Natiuretic Peptide, Subclinical Atherosclerosis and Prognosis", The Online Abstract Submission and Invitation System, Circulation, vol. 114, No. 18, Suppl. S. Oct. 2006, 725-726 XP008084065 & 79th Annual Scientific Session of the American Heart Association, Chicago, IL, USA 2006, ISSN: 0009-7322.

Reilly et al., "Plasma Cytokines, Metabolic Syndrome and Atherosclerosis in Humans", Journal of Investigative Medicine, vol. 55; 2007, 26-35.

Reith et al., "Procalcitonin in Early Detection of Postoperative Complications", Digestive Surgery, vol. 15, No. 3; 1998, 260-265.

Schlitt et al., "CD14 + CD16 + monocytes in coronary artery disease and their relationship to serum TNF-α levels", Thromb Haemost, vol. 92; 2004, 419-424.

Schnabel et al., "Analysis of N-terminal-pro-brain natriuretic peptide and C-reactive protein for risk stratification in stable and unstable coronary artery disease: results from the AtheroGene Study", European Heart Journal, vol. 26, No. 3; 2005, 241-249.

Schwarz, et al., "Serum procalcitonin levels in bacterial and abacterial meningitis", Crit Care Med, vol. 28, No. 6; 2000, 1828-1832.

Senturk et al., "Procalcitonin in patients with acute coronary syndrome: correlation with high-sensitive C-reactive protein, prognosis and severity of coronary artery disease", Acta Cardiologica, vol. 62; 2007, 135-141.

Stolz et al., "Antibiotic Treatment of Exacerbations of COPD", Chest, vol. 131; 2007, 9-19.

Tipping et al., "Production of Tumor Necrosis Factor and Interleukin-1 by Macrophages from Human Atheromatous Plaques", American Journal of Pathology, vol. 142, No. 6; 1993, 1721-1728.

Wanner et al., "Relationship between procalcitonin plasma levels and severity of injury, sepsis, organ failure, and mortality in injured patients", Crit Care Med, vol. 28, No. 4; 2000, 950-957.

Wiedermann et al., "Migration of human monocytes in response to procalcitonin", Crit Care Med, vol. 30, No. 5; 2002, 1112-1117.

Wunder et al., "Are IL-6, IL-10 and PCT plasma concentrations reliable for outcome prediction in severe sepsis? A comparison with APACHE III and SAPS II", Inflammation Research, vol. 53; 2004, 158-163.

Yusuf et al., "Effect of potentially modifiable risk factors associated with myocardial infarction in 52 countries (The INTERHEART Study): case-control study", Lancet, vol. 364; 2004, 937-952.

International Preliminary Report on Patentability for corresponding PCT/EP2008/006378.

METHOD FOR RISK STRATIFICATION IN STABLE CORONARY ARTERY DISEASE

CROSS-REFERENCE TO RELATED APPLICATION

This application is a divisional application of copending U.S. application Ser. No. 12/671,823 filed Feb. 2, 2010 as a 371 filing of PCT International application no. PCT/EP2008/006378 filed Aug. 1, 2008 and published in English as WO 2009/018979 A1 on Feb. 12, 2009, which claims the priority of European application no. 07015271.5 filed Aug. 3, 2007. The disclosures of these applications and all other patents, published applications and other references cited herein are hereby incorporated by reference in their entirety.

BACKGROUND OF THE INVENTION

The present invention discloses a new method for patient stratification in stable coronary disease (coronary disease: CAD) according to the patients' individual cardiac risks. Patients in the condition of a stable CAD are typically patients with angiographically proven CAD, i.e. with affected coronary arteries, with plaques on the inner walls of the coronary artery (atherosclerosis) and stenosis in a major coronary artery. CAD is considered a serious cardiac risk. CAD patients are considered as "stable" if the CAD does not manifest itself in the form of acute cardiovascular events.

In view of the imminent risk of future cardiovascular events it would be highly desirable to be able to distinguish within the group of patients with stable CAD between different groups according to their personal cardiac risk such that an "individual state of alert" can be determined for a particular patient in accordance with the risk group to which he has been allotted. Such grouping of patients is usually called "stratification".

Distinguishing high risk patients from patients at moderate or low risk would allow a better selection of the most appropriate therapeutic strategy for a particular patient, avoiding, for example, underestimation of the cardiac risk and undermedication of high risk patients on the one hand and unnecessary therapeutic interventions, and the associated costs, with low risk patients on the other.

It is, therefore, an object of the present invention to provide a new method by which patients with stable CAD can be stratified in accordance with their personal cardiac risks, i.e. with respect to their individual risks concerning the future incidence of cardiovascular events.

As is further explained in detail below, the inventors have conducted a study to evaluate the potential usefulness of a number of analytes (biomolecules, biomarkers) which can be determined in the circulation of patients for a stratification of patients with stable CAD.

In the course of said study they have surprisingly found that a highly sensitive measurement of the concentration of the peptide procalcitonin (PCT) in the circulation of CAD patients in the range of very low physiological concentrations, which concentrations up to now were considered as being below diagnostic significance and, therefore, concentrations typical for normal healthy individuals, allows a useful stratification of CAD patients, and that the usefulness of such highly sensitive PCT determination can even be increased if the results obtained fro PCT are evaluated in combination with the results of the measurement of an analyte of another type action (a vasoactive analyte), exemplified by the so-called B-type (or brain) natriuretic peptide BNP.

Accordingly, the present inventions discloses a method as claimed in any of claims 1 to 6, and the use of a highly sensitive determination of PCT in the context of the prognosis of cardiovascular diseases for the risk stratification of patients, especially in arteriosclerosis and CAD, according to claims 7 and 8 respectively.

Procalcitonin (PCT), which is to be measured in accordance with the present invention, has become a well-established biomarker for sepsis diagnosis: PCT reflects the severity of bacterial infection and is in particular used to monitor progression of infection into sepsis, severe sepsis, or septic shock. It is possible to use PCT to measure the activity of the systemic inflammatory response, to control success of therapy, and to estimate prognosis (1) (2) (3) (4) (5). The increase of PCT levels in patients with sepsis correlates with mortality (6).

Whereas an increasing number of studies investigates the potential role of PCT in other infectious diseases like pneumonia, bacterial meningitis and malaria (7) (8) (9), no studies reported yet about the potential use of PCT in risk stratification of patients suffering from stable coronary artery disease (CAD). In vitro-studies showed, that PCT plays an important role during monocyte adhesion and migration and further has an effect on inducible nitric oxide synthase (iNOS) gene expression (10) (11) (12). The association between PCT levels and low-grade inflammation of the arterial wall in atherosclerosis and the potential effect on endothelial dysfunction has not been analyzed. Our prospective study examined the prognostic impact of PCT in a large group of consecutively enrolled stable angina patients on cardiovascular outcome to evaluate the potential clinical applicability of PCT measurements in CAD.

In the context of sepsis and related conditions, where the concentrations of PCT reach rather high physiological concentrations, PCT has been measured traditionally by means of an assay of the sandwich type using two monoclonal antibodies binding to different portions of the PCT molecule so that essentially only the complete PCT molecule is detected (see, for example, (1)). The typical functional assay sensitivity (FAS) of the typical two-sided chemiluminescence assay for PCT is 300 ng/L (0.3 ng/ml or 0.3 µg/L).

More recently new highly sensitive assays for the determination of PCT have been developed (28). The functional assay sensitivity (FAS, interassay CV<20%) of this new assay was <7 ng/1 PCT. Using this assay, typical PCT concentrations in healthy individuals could be determined. In 500 healthy individuals the range was <7 to 63 ng/L (<0.007 to 0.063 ng/ml), i.e. a range of concentrations well below 0.1 ng/ml. The determined median was 13.5 ng/L (95% confidence interval for the mean 12.6 to 14.7 ng/L).

In further improved form said sensitive PCT assay is available as PCT sensitive LIA (B.R.A.H.M.S AG, Hennigsdorf, Germany) having an analytical assay sensitivity of 0.01 ng/ml and a functional assay sensitivity (FAS) of at least 0.05 ng/ml. A related assay for the time-resolved amplified cryptate emission (TRACE) technology (Kryptor PCT, B.R.A.H.M.S AG, Hennigsdorf) has a functional assay sensitivity of 0.06 µg/L (0.06 ng/ml).

The more recent sensitive PCT assays have predominantly been used in connection with the guidance of antibiotic therapy in lower respiratory tract infections (community-acquired pneumonia, CAP; exacerbations of chronic obstructive pulmonary disease, COPD: see (29), (30), (31)). In the case of CAP antibiotic treatment is recommended on the basis of measured PCT concentrations as follows: strongly encouraged, greater than 0.5 µg/L; encouraged, greater than 0.25 µg/L; discouraged, less than 0.25 mg/L; strongly discouraged, less than 0.1 µg/L (29). In other words, concentrations of 0.1 µg/L (or 0.1 ng/ml) are considered as concentrations typical for healthy individuals.

The method of risk stratification of patients with stable coronary artery disease (stable CAD) is based on a differential evaluation of measured PCT concentrations which are below the value of 0.1 ng/ml for healthy individuals and which so far have not been used for diagnostic of prognostic purposes.

The invention is discussed in more detail in the following sections and the FIGS. 1 to 3 and Tables 1 to 7 mentioned therein. The Tables mentioned are found on separate pages at the end of the text of the description.

DETAILED DESCRIPTION OF THE INVENTION

Study Population

Figure 1:
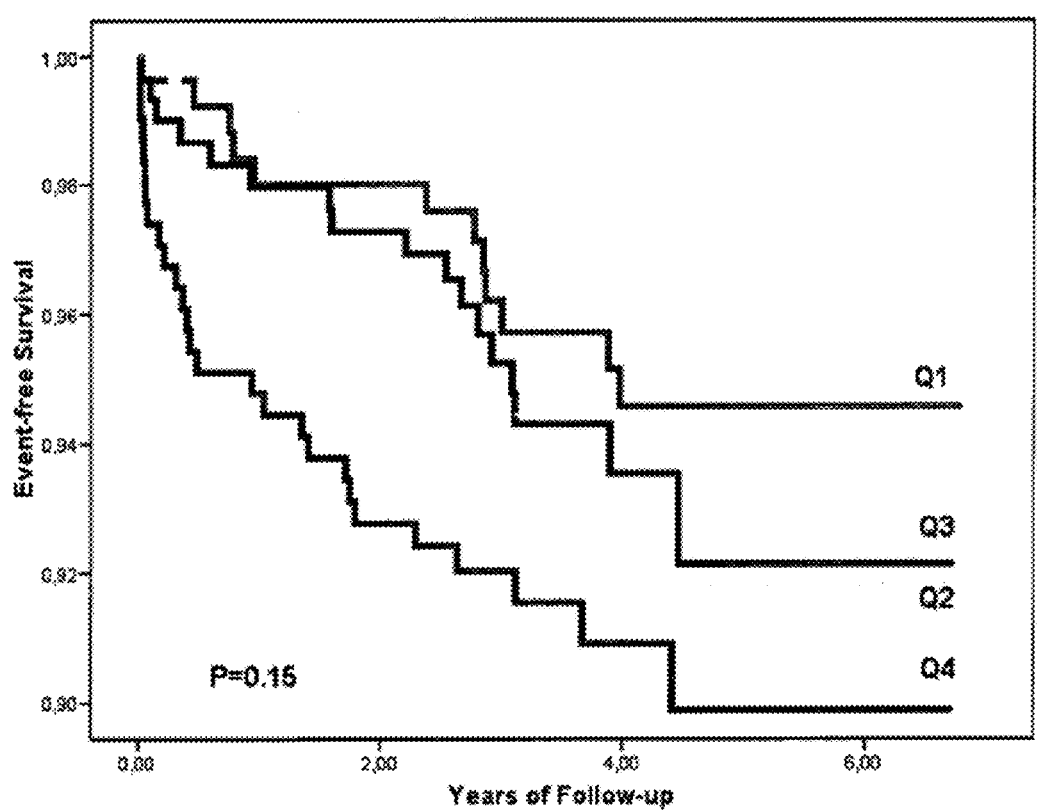
FIG. 1: shows Kaplan-Meier survival curves showing cardiovascular events according to quartiles of procalcitonin.

Between November 1996 and January 2004, 3326 patients with angiographically proven CAD and at least one stenosis ≥30% diagnosed in a major coronary artery at the Department of Medicine II of the Johannes Gutenberg University in Mainz or the Department of Medicine of the German Federal Armed Forces Central Hospital in Koblenz were enrolled in the Athero Gene registry. Further details on the concept of the AtheroGene study have been described previously (13).

In the present substudy, exclusion criteria were clinical signs of acute coronary syndrome (unstable Angina Braunwald classification class B or C, acute ST-segment elevation, and non-ST-segment elevation myocardial infarction). Patients with coronary artery bypass surgery or coronary revascularization during the last four weeks were also excluded. Further reasons for exclusion were evidence of hemodynamically significant valvular heart disease, surgery or trauma within the previous month, known cardiomyopathy, manifest carcinoma, chronic inflammatory disease, febrile conditions, or use of oral anticoagulant therapy within the previous four weeks.

The history of classical risk factors was assessed as follows. Patients receiving anti-hypertensive treatment or having already confirmed the diagnosis of hypertension (blood pressure above 160/90 mmHg) were considered to have hypertension. Hyperlipoproteinemia was diagnosed in patients under lipid-lowering medication or with a history of cholesterol levels ≥240 mg per deciliter. Patients were classified as currently smoking, as having smoked in the past (if they had stopped more than 4 weeks and less than 40 years earlier), or as having never smoked (if they had never smoked or had stopped 40 or more years earlier). We considered patients receiving dietary treatment or medication for diabetes or whose current fasting blood glucose level was above 125 mg per deciliter to suffer from diabetes mellitus.

1124 patients were followed up during a median period of 3.8 (maximum 6.8) years. Patients either presented themselves at our clinic (78.2%) or were interviewed by telephone by trained medical staff. Follow-up information, including death from cardiovascular causes (n=40), death from causes not related to coronary artery disease (n=30), and non-fatal myocardial infarction (n=32), was obtained from hospital or general-practitioner charts. The primary endpoint was non-fatal myocardial infarction and cardiovascular death.

The AtheroGene study was approved by the local ethics committee of the University of Mainz. Study participants had German nationality and, particularly, were inhabitants of the Rhein-Main-Area. All patients were caucasian. Participation was voluntary, and patients were enrolled after written informed consent was obtained.

Laboratory Methods

Blood samples were drawn under standardized conditions before performance of coronary angiography. Samples were taken when patients entered the catheterization lab after a minimum 12 h-fast. Serum lipid levels were measured immediately. Lipid levels were measured using routine methods (total cholesterol and triglycerides, Roche Diagnostics GmbH, Mannheim, Germany; high-density lipoprotein cholesterol, Rolf Greiner Biochemica, Mannheim, Flacht bei Limburg, Germany; and low-density lipoprotein cholesterol calculated according to the Friedewald formula). The LDL-/HDL-ratio was computed by dividing LDL by HDL levels.

Plasma and serum samples were centrifuged at 4000 g for 10 minutes, divided into aliquots, and stored at −80° C. until analysis. PCT was determined by a highly sensitive immunoluminometric assay (B.R.A.H.M.S PCT sensitive; B.R.A.H.M.S AG, Hennigsdorf, Germany; analytical assay sensitivity: 0.01 ng/ml; functional assay sensitivity (20% inter-assay variation coefficient): 0.05 ng/ml). Data were generated using one lot of chemicals. C-reactive protein (CRP) was analyzed by a latex particle-enhanced immunoassay (Roche Diagnostics, Mannheim, Germany; detection range: 0.1 to 20 mg/l; interassay coefficient of variation, 1.0 percent for values of 15 mg per liter and 6.5 percent for values below 4 mg per liter). Plasma B-type natriuretic peptide (BNP) was determined using a fluorescence immunoassay (Biosite, San Diego, Calif., USA; detection range: 5 to 5000 pg/ml; interassay coefficient of variation of near 10%; negligible cross-reactivity with other natriuretic peptides). All laboratory measurements were performed in a blinded fashion without knowledge of the clinical status of the patient.

Statistical Considerations

The mean values (±standard deviation) and proportions of baseline cardiovascular risk factors, clinical variables, and biomarkers were calculated for study participants according to quartiles of procalcitonin. Due to the small range of the procalcitonin levels, the quartiles comprise not the same number of patients. Variables with a skewed distribution (|skewness|>1) were presented as medians with quartiles. Correlation analysis was done by Spearman rank correlation. In another analysis hazard ratios for the highest versus other quartiles of PCT were dichotomized according to classical risk factors or medians of clinical variables and biomarkers.

The association of the biomarkers PCT and BNP with the primary endpoint according to quartiles was analyzed in different models by Cox regression analysis, the first model adjusting for age and sex and the second adjusting for the potential confounders and classical risk factors (age, sex, body-mass index, hypertension, diabetes mellitus, smoking status, LDL-/HDL-ratio, number of diseased vessels, beta-blocker and statin therapy). The cumulative event plots according to quartiles of PCT concentration were estimated by the Kaplan-Meier method and were compared by use of the log rank test. All survival analyses were conducted for the primary end point of non-fatal myocardial infarction or cardiovascular death. Data of patients who died from causes not related to cardiovascular disease were censored at the time of death.

PCT and BNP were log-transformed to enhance model fit. To compare the predictive power of these biomarkers, hazard ratios per one standard deviation increment were calculated in univariate and multivariate analysis (adjusted for classical risk factors and clinical variables). A backward stepwise Cox regression approach was taken for the multivariate analyses with P=0.10 as the critical value for entering and excluding ten variables (age, sex, body-mass index, hypertension, diabetes, smoking, LDL-/HDL-ratio, number of diseased vessels, statin and beta-blocker therapy) in the model.

Hazard ratios (HR) and 95% confidence interval (CI) are reported with 2-tailed probability values. Proportional hazards assumption was checked using standard methods based on testing for significant slope of the smooth curve through the scatter of the rescaled Schoenfeld residuals versus time.

To further assess the predictive ability of the models, the inventors considered the cardiovascular endpoint at two years as a binary variable and logistic regression was performed. Associated receiver operating characteristic (ROC) curves for predicted probabilities were drawn for a basic model containing classical risk factors and models additionally containing PCT, CRP and BNP. The corresponding areas under the curve along with 95% CI were calculated.

The inventors further evaluated the combined role of PCT and BNP on cardiovascular risk and therefore tested for interaction followed by a dichotomized analysis of both variables by using the highest quartile as cut-off point. Hazard ratios and 95% CI, along with P-values, were reported. Another cumulative event plot was estimated by the Kaplan-Meier method for these four subgroups and compared using the log rank test.

As P-values are not adjusted for multiple testing, they have to be considered as descriptive. All calculations were carried out using SPSS 15.0 for Windows, version 15.0.1 (SPSS Inc., Chicago, Ill., USA).

Results

The mean age of the study population was 61.3±9.5 years, and 80.5% of the patients were male. The patients in the present substudy were divided into four groups according to quartiles of PCT levels (00Table 1). No significant differences for the distribution of the classical risk factors were found. CRP levels were higher in the fourth quartile than in the others (3.66 mg/l vs. 1.81-2.10 mg/l). A moderate correlation between PCT and CRP (r=0.27) was found.

The inventors further evaluated the predictive value of PCT in subgroup analysis (Table 2). Median levels were used to dichotomize continuous variables. In particular, PCT levels were strongly predictive in patients with BNP serum concentration above the median of 37.48 pg/ml with a 2.41-fold increased risk (95% CI 1.32-4.42; P=0.004) for the highest PCT quartile.

Table 3 outlines the association between PCT, CRP and BNP with future cardiovascular events. The percentage of events increased across quartiles (FIG. 1) such as patients in the highest quartile of PCT were associated with an 2.27-fold (95% CI: 1.14-4.51; P=0.02) increase in risk for future cardiovascular events in age- and sex-adjusted model. This association remained significant in models adjusting for most potential confounders. If analyzed as continous variable, an increment of one standard deviation (SD) of PCT revealed a 1.33 higher (95% CI: 1.02-1.74; P=0.04) risk for future cardiovascular events. Levels of BNP have been related independently to the primary endpoint, whereas no significant association between CRP and cardiovascular outcome could be observed in the fully adjusted model.

All classical risk factors and clinical variables were entered in a backward multiple stepwise regression analysis as outlined in table 4. Continous variables were log-transformed and have been treated per increment of one SD. PCT (HR 1.30, 95% CI: 1.00-1.70; P=0.05) was selected as an independent predictor of cardiovascular risk. The final model also revealed LDL-/HDL-ratio, female gender and insulin-dependent diabetes mellitus (IDDM) as predictors for the primary endpoint.

Figure 2:
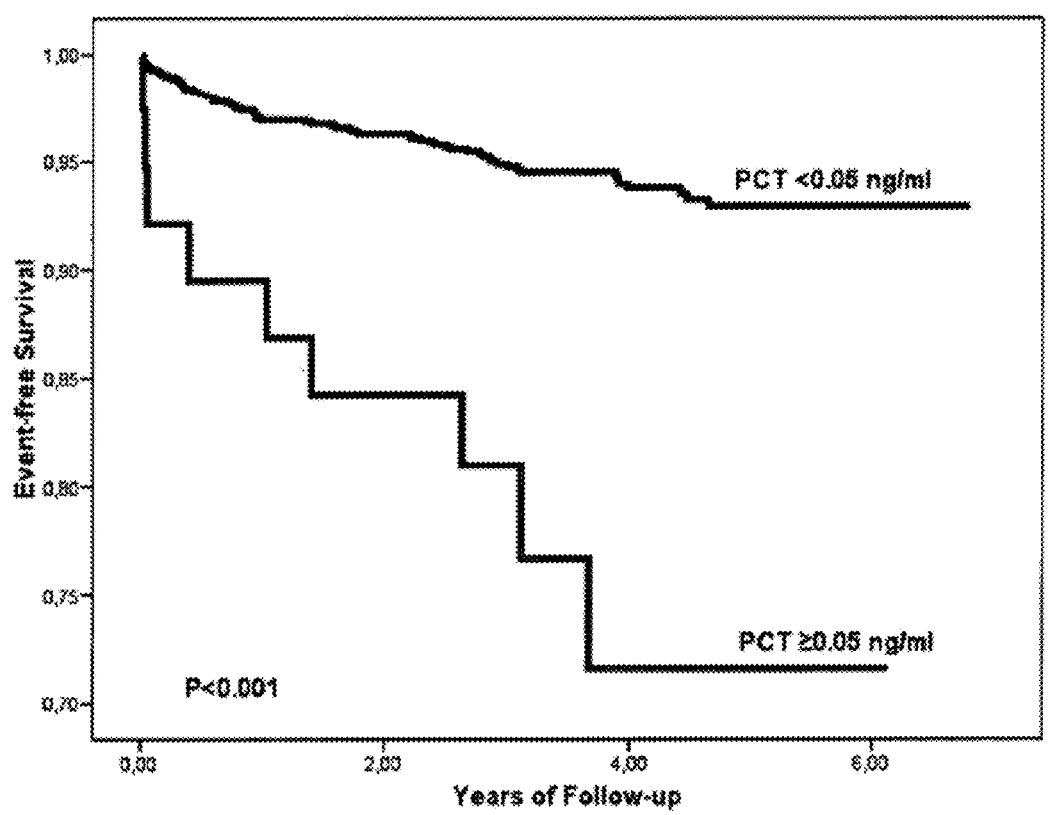
FIG. 2: shows Kaplan-Meier survival curves showing cardiovascular events according to procalcitonin cut-off value 0.05 ng/ml.

In another subanalysis, a PCT level of 0.05 ng/ml (according to the functional assay sensitivity) was chosen as cut-off value for cardiovascular risk prediction. 25% of the 39 patients with PCT levels above 0.05 ng/ml experienced cardiovascular events and had a significant poorer prognosis (FIG. 2). When entered in a backward multiple stepwise regression analysis, a PCT level above 0.05 ng/ml is associated with a 4.22 higher (95% CI: 2.07-8.59; P<0.001) cardiovascular risk (Table 5).

To further explore whether PCT and BNP added information beyond that obtained from classical risk factors, the inventors computed the area under the ROC curve (AUC) associated with prediction of different logistic regression models, considering the cardiovascular endpoint at 2 years as a binary variable (Table 6). As there were patients with a follow-up of less than 2 years, only 1057 patients were available for this analysis; 46 of them experienced a cardiovascular event. The basic model including classical risk factors such as age, sex, BMI, hypertension, diabetes mellitus, smoking status, LDL-/HDL-ratio, number of diseased vessels, beta-blocker and statin therapy revealed an AUC of 0.74 (95% CI: 0.67-0.81). Table 6 presents analyses comparing this basic model with models additionally including either PCT, or BNP, or two, or all of them. Inclusion of one SD increase of PCT improved the predictive value of the basic model, reporting an increase from 0.74 to 0.77. One SD increase of BNP revealed most additional information beyond application of the basic model. The combination of BNP and PCT with the basic model resulted in the highest prognostic accuracy of this model. Results were similar during a 1-year and 3-year follow-up (data not shown).

Figure 3:
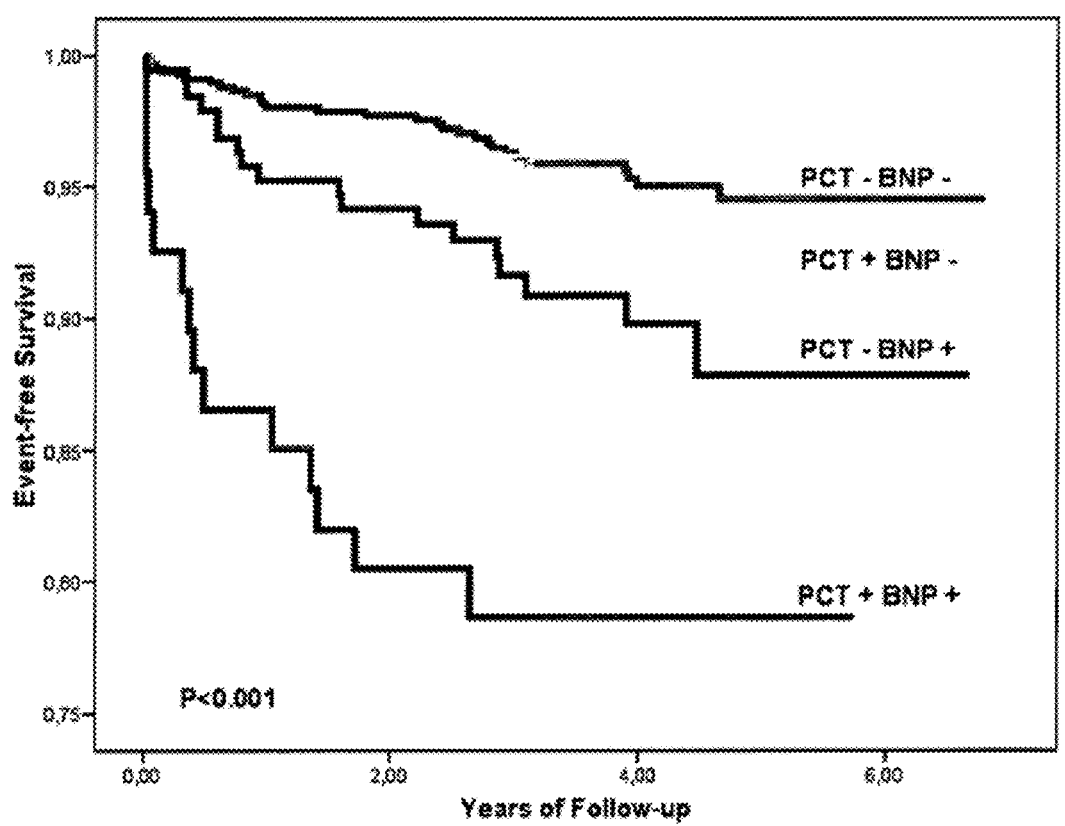
FIG. 3: Kaplan-Meier survival curves showing cardiovascular events according to procalcitonin and B-type natriuretic peptide in combined analysis.

Because of the strong predictive value of PCT in patients with BNP levels above the median (Table 2) and the high prognostic accuracy for cardiovascular events when BNP and PCT were combined in a model with classical risk factors (Table 6), the inventors finally explored to what extent PCT might add to the prognostic value of BNP (Table 7). With the test for interaction being negative (P=0.78), the inventors assumed an additive effect for both biomarkers. Patients with elevated levels of both biomarkers in the upper quartile were at the highest risk for future cardiovascular events (HR 7.04; 95% CI: 3.40-14.57; P<0.001). FIG. 3 provides the Kaplan-Meier survival curves according to levels of PCT and BNP in combined analysis.

DISCUSSION

In this prospective cohort of patients with angiographically documented CAD an independent association of PCT with future cardiovascular events has been demonstrated. This association did not change appreciably after adjustment for most potential confounders, indicating that PCT provides important information about cardiovascular prognosis in addition of classical risk factors and other clinical variables. Combined analysis of PCT and BNP improved the prognostic accuracy for future cardiovascular events in the present study.

Yet, only two studies evaluated the potential use of PCT in the setting of CAD. Erren et al. (14) found slightly increased PCT levels only in CAD patients with additional peripheral arterial disease (PAD) and discussed PCT as a marker for the atherosclerotic burden in a multi-marker approach.

Ilhan et al. (15) found higher PCT levels (0.40±0.04 ng/ml as opposed to 0.19±0.02 ng/ml in the control group) among CAD patients experiencing a cardiovascular event. Herein the inventors demonstrated PCT as an independent predictor of future cardiovascular events, in particular adding information on patients with high BNP levels, indicating a potential of PCT to better stratify in high risk individuals.

Local or systemic inflammation affecting certain types of tissue, also a trauma-related host response (16) (17) (18) (19) (20), and consecutive monocytic activation thus are a prerequisite for PCT production (4). The expression of PCT messenger-RNA by peripheral blood mononuclear cells (21) is stimulated in vitro not only by lipopolysaccharides, but also by the proinflammatory cytokines interleukin-1β (IL-1β), interleukin-2 (IL-2), interleukin-6 (IL-6) and tumor necrosis factor-a (TNF-α), which seem to play a pivotal role in the atherosclerotic process (22) (23) (24) (25). Thus, slightly increased PCT levels might be an epiphenomenon of the inflammatory activity within the vascular wall caused by atherosclerosis. However, PCT seems to play a causative role in monocytic activation: as a chemoattractant initially only produced in adherent monocytes, which recruit later parenchymal cells of the inflammated tissue for further PCT production. Thus, PCT could have also an effect on leukocyte migration (4) (10) (11) (14). Further studies have to investigate, if the in vitro demonstrated stimulating effect of PCT on nitric oxide synthesis gene expression (12) also has an influence on endothelial dysfunction caused by atherosclerosis.

In the present study, patients with combined elevation of PCT and BNP levels in the upper quartile had a 7.0-fold increased risk for the primary endpoint compared to a 3.2-fold increased risk when BNP was elevated alone. Thus, PCT significantly improved the AUC of the basic model (classical risk factors) for risk prediction and even obtained additional information on top of the biomarker BNP.

BNP is an established marker for left ventricular dysfunction. The sepsis marker PCT might also be a marker for low-grade inflammation, in particular for monocyte activation or endothelial dysfunction, as shown in several in vitro-studies. The representation of two different pathomechanisms by BNP and PCT would explain the improvement of the prognostic accuracy for future cardiovascular events. Further studies are needed to evaluate the role of PCT for risk prediction in diseases other than severe bacterial infections and to elucidate more its pathophysiological role in the inflammatory cascade.

As the choice of the cutoffs for the analyses in table 7 and FIG. 3 is data driven, the results can only give hints, but have to be validated in independent studies.

In conclusion, PCT is independently related to future cardiovascular events in a population of CAD patients and might add information for risk stratification, in particular, in high risk individuals.

SUMMARY

Background:

Procalcitonin (PCT) is a well-established biomarker for the diagnosis and therapeutic monitoring of sepsis. In vitro-studies showed that PCT has an effect on monocyte activation and even on nitric oxide synthesis. The present prospective study examined the prognostic impact of PCT in patients with established coronary artery disease (CAD) on cardiovascular outcome.

Methods:

In a substudy of the prospective Athero Gene survey, in 1124 patients with stable CAD, the risk of cardiovascular death and non-fatal myocardial infarction (N=72) over a median follow-up of 3.8 (maximum 6.8) years according to the baseline concentration of PCT has been assessed.

Results:

The age- and sex-adjusted hazard ratio for patients within the highest quartile of PCT related a 2.27-fold increase (95% confidence interval (CI): 1.14-4.51; P=0.02) of the relative risk for cardiovascular death and non-fatal myocardial infarction, when compared to the first quartile. Adjustment for classical risk factors and clinical variables did not attenuate this relationship. Inclusion of one standard deviation increase of PCT improved the predictive value of a basic model (classical risk factors) for cardiovascular risk prediction monitored by the area under the curve (AUC) of an % CI: 3.40-14.57; P<0.001) higher cardiovascular risk.

CONCLUSIONS

Baseline concentration of PCT is independently related to future cardiovascular events in patients with stable CAD

REFERENCES

1. Assicot M, Gendrel D, Carsin H, Raymond J, Guilbaud J, Bohuon C. High serum procalcitonin concentrations in patients with sepsis and infection. Lancet 1993; 341:515-8.
2. Clec'h C, Ferriere F, Karoubi P, et al. Diagnostic and prognostic value of procalcitonin in patients with septic shock. Crit Care Med 2004; 32:1166-9.
3. Lee Y J, Park C H, Yun J W, Lee Y S. Predictive comparisons of procalcitonin (PCT) level, arterial ketone body ratio (AKBR), APACHE III score and multiple organ dysfunction score (MODS) in systemic inflammatory response syndrome (SIRS). Yonsei Med J 2004; 45:29-37.
4. Meisner M. Biomarkers of sepsis: clinically useful? Curr Opin Crit Care 2005; 11:473-80.
5. Wunder C, Eichelbronner O, Roewer N. Are IL-6, IL-10 and PCT plasma concentrations reliable for outcome prediction in severe sepsis? A comparison with APACHE III and SAPS II. Inflamm Res 2004; 53:158-63.
6. Oberhoffer M, Vogelsang H, Russwurm S, Hartung T, Reinhart K. Outcome prediction by traditional and new markers of inflammation in patients with sepsis. Clin Chem Lab Med 1999; 37:363-8.
7. Bugden S A, Coles C, Mills G D. The potential role of procalcitonin in the emergency department management of febrile young adults during a sustained meningococcal epidemic. Emerg Med Australas 2004; 16:114-9.
8. Chiwakata C B, Manegold C, Bonicke L, Waase I, Julch C, Dietrich M. Procalcitonin as a parameter of disease severity and risk of mortality in patients with *Plasmodium falciparum* malaria. J Infect Dis 2001; 183:1161-4.
9. Schwarz S, Bertram M, Schwab S, Andrassy K, Hacke W. Serum procalcitonin levels in bacterial and abacterial meningitis. Crit Care Med 2000; 28:1828-32.
10. Linscheid P, Seboek D, Schaer D J, Zulewski H, Keller U, Muller B. Expression and secretion of procalcitonin and calcitonin gene-related peptide by adherent monocytes and by macrophage-activated adipocytes. Crit Care Med 2004; 32:1715-21.

11. Wiedermann F J, Kaneider N, Egger P, et al. Migration of human monocytes in response to procalcitonin. Crit Care Med 2002; 30:1112-7.
12. Hoffmann G, Czechowski M, Schloesser M, Schobersberger W. Procalcitonin amplifies inducible nitric oxide synthase gene expression and nitric oxide production in vascular smooth muscle cells. Crit Care Med 2002; 30:2091-5.
13. Blankenberg S, Rupprecht H J, Bickel C, et al. Glutathione peroxidase 1 activity and cardiovascular events in patients with coronary artery disease. N Engl J Med 2003; 349:1605-13.
14. Erren M, Reinecke H, Junker R, et al. Systemic inflammatory parameters in patients with atherosclerosis of the coronary and peripheral arteries. Arterioscler Thromb Vasc Biol 1999; 19:2355-63.
15. Ilhan F, Akbulut H, Karaca I, Godekmerdan A, Ilkay E, Bulut V. Procalcitonin, c-reactive protein and neopterin levels in patients with coronary atherosclerosis. Acta Cardiol 2005; 60:361-5.
16. Meisner M, Tschaikowsky K, Hutzler A, Schick C, Schuttler J. Postoperative plasma concentrations of procalcitonin after different types of surgery. Intensive Care Med 1998; 24:680-4.
17. Meisner M, Rauschmayer C, Schmidt J, et al. Early increase of procalcitonin after cardiovascular surgery in patients with postoperative complications. Intensive Care Med 2002; 28:1094-102.
18. Meisner M, Adina H, Schmidt J. Correlation of procalcitonin and C-reactive protein to inflammation, complications, and outcome during the intensive care unit course of multiple-trauma patients. Crit Care 2006; 10:R1.
19. Wanner G A, Keel M, Steckholzer U, Beier W, Stocker R, Ertel W. Relationship between procalcitonin plasma levels and severity of injury, sepsis, organ failure, and mortality in injured patients. Crit Care Med 2000; 28:950-7.
20. de Werra I, Jaccard C, Corradin S B, et al. Cytokines, nitrite/nitrate, soluble tumor necrosis factor receptors, and procalcitonin concentrations: comparisons in patients with septic shock, cardiogenic shock, and bacterial pneumonia. Crit Care Med 1997; 25:607-13.
21. Oberhoffer M, Stonans I, Russwurm S, et al. Procalcitonin expression in human peripheral blood mononuclear cells and its modulation by lipopolysaccharides and sepsis-related cytokines in vitro. J Lab Clin Med 1999; 134:49-55.
22. Mackay F, Loetscher H, Stueber D, Gehr G, Lesslauer W. Tumor necrosis factor alpha (TNF-alpha)-induced cell adhesion to human endothelial cells is under dominant control of one TNF receptor type, TNF-R55. J Exp Med 1993; 177:1277-86.
23. Reilly M P, Rohatgi A, McMahon K, et al. Plasma cytokines, metabolic syndrome, and atherosclerosis in humans. J Investig Med 2007; 55:26-35.
24. Schlitt A, Heine G H, Blankenberg S, et al. CD14+CD16+ monocytes in coronary artery disease and their relationship to serum TNF-alpha levels. Thromb Haemost 2004; 92:419-24.
25. Tipping P G, Hancock W W. Production of tumor necrosis factor and interleukin-1 by macrophages from human atheromatous plaques. Am J Pathol 1993; 142:1721-8.
26. Pischon T, Girman C J, Sacks F M, Rifai N, Stampfer M J, Rimm E B. Non-high-density lipoprotein cholesterol and apolipoprotein B in the prediction of coronary heart disease in men. Circulation 2005; 112:3375-83.
27. Yusuf S, Hawken S, Ounpuu S, et al. Effect of potentially modifiable risk factors associated with myocardial infarction in 52 countries (the INTERHEART study): case-control study. Lancet 2004; 364:937-52.
28. Nils G. Morgenthaler et al., Sensitive Immunoluminometric Assay for the Detection of Procalcitonin. Clinical Chemistry 48, No. 5, 2002; 788-790.
29. Mirjam Christ-Crain et al., Procalcitonin Guidance of Antibiotic Therapy in Community-acquired Pneumonia. American Journal of Respiration and Critical Care Medicine, VOl. 174; 2006; 84-93.
30. Diana Stolz et al., Antibiotic treatment of Exacerbations of COPD. Chest 131, 1, January 2007: 9-19.
31. Mirjam Christ-Crain et al., Effect of procalcitonin-guided tretament on antibiotic use and outcome in lower respiratory tract infections; cluster-randomised, single-blinded intervention trial. Lancet 2004, 363: 600-607

TABLE 1

Baseline characteristics of the study population according to quartiles

| Characteristic | Q1 (N = 254) | Q2 (N = 259) | Q3 (N = 301) | Q4 (N = 310) |
| --- | --- | --- | --- | --- |
| Procalcitonin (ng/ml) | <0.010 | 0.010-0.013 | 0.014-0.020 | >0.020 |
| Age (yrs) | 60.6 ± 10.0 | 60.5 ± 10.0 | 61.3 ± 9.5 | 62.5 ± 8.6 |
| Male sex (%) | 72.0 | 80.3 | 86.0 | 82.3 |
| Traditional risk factors | | | | |
| Body-mass index (kg/m$^2$) | 27.0 ± 4.0 | 27.4 ± 3.8 | 27.9 ± 3.7 | 28.4 ± 4.1 |
| Hypertension (%) | 80.3 | 75.7 | 79.1 | 83.2 |
| Diabetes mellitus | | | | |
| Dietetic treatment (%) | 4.3 | 2.7 | 3.7 | 6.1 |
| Drug treatment (%) | 7.5 | 8.1 | 10.3 | 11.3 |
| Insulin dependent (%) | 8.7 | 5.8 | 6.6 | 12.9 |
| Smoking Status | | | | |
| Never smoked (%) | 37.8 | 37.8 | 38.2 | 32.3 |
| Ex-smoker (%) | 42.9 | 44.4 | 46.2 | 51.3 |
| Current smoker (%) | 19.3 | 17.8 | 15.6 | 16.5 |
| Lipid status | | | | |
| LDL cholesterol (mg/dl) | 128.0 (98.0-157.8) | 123.0 (94.0-144.0) | 118.0 (92.5-143.0) | 119.0 (95.8-150.0) |

TABLE 1-continued

Baseline characteristics of the study population according to quartiles

| Characteristic | Q1 (N = 254) | Q2 (N = 259) | Q3 (N = 301) | Q4 (N = 310) |
|---|---|---|---|---|
| HDL cholesterol (mg/dl) | 53.0 (43.0-64.0) | 49.0 (43.0-58.0) | 47.0 (40.5-56.0) | 45.0 (39.0-55.0) |
| Triglycerides (mg/dl) | 122.0 (93.8-168.0) | 117.0 (88.0-156.0) | 129.0 (97.0-188.0) | 148.0 (103.0-201.5) |
| Clinical variables | | | | |
| Multi-vessel disease (%) | 74.4 | 67.2 | 72.4 | 72.9 |
| History of myocardial infarction (%) | 42.5 | 44.4 | 47.5 | 38.1 |
| Left ventricular ejection fraction (%) | 65.0 (53.5-73.0) | 69.5 (60.0-77.0) | 66.0 (55.0-74.0) | 70.0 (58.0-78.0) |
| Medication | | | | |
| Beta-blocker (%) | 58.7 | 62.2 | 70.8 | 62.3 |
| Statin (%) | 53.1 | 51.8 | 61.4 | 56.8 |
| ACE-inhibitor (%) | 62.2 | 55.6 | 58.8 | 59.0 |
| Biomarkers | | | | |
| C-reactive protein (mg/l) | 1.85 (0.97-3.79) | 1.81 (0.98-4.18) | 2.10 (1.17-4.02) | 3.66 (1.76-8.15) |
| B-type natriuretic peptide (pg/ml) | 38.97 (13.79-98.87) | 40.94 (11.86-92.80) | 37.64 (12.02-102.15) | 33.97 (9.88-101.11) |

Data presented are percentage of patients, mean±standard deviation, or median and $25^{th}/75^{th}$ interquartile range for skewed (|skewness|>1) variables. Left-ventricular ejection fraction was available for 818 patients and B-type natriuretic peptide for 1032 patients. LDL denotes low-density lipoprotein, HDL high-density lipoprotein. To convert values for cholesterol to millimoles per liter, multiply by 0.02586; to convert values for triglycerides to millimoles per liter, multiply by 0.01129.

TABLE 2

Hazard ratios (95% confidence interval) for highest versus other quartiles of procalcitonin according to traditional risk factors (age- and sex-adjusted)

| Variable | | HR (95% CI) | P-value |
|---|---|---|---|
| Age* | ≤63 yrs | 1.92 (0.98-3.78) | 0.06 |
| | >63 yrs | 1.56 (0.77-3.13) | 0.21 |
| Sex** | Female | 1.81 (0.73-4.51) | 0.20 |
| | Male | 1.72 (0.97-3.06) | 0.07 |
| Body-mass index | ≤26.4 kg/m² | 2.22 (0.98-5.01) | 0.06 |
| | >26.4 kg/m² | 1.54 (0.83-2.83) | 0.17 |
| Hypertension | No | 1.16 (0.38-3.53) | 0.80 |
| | Yes | 1.98 (1.14-3.43) | 0.02 |
| Diabetes mellitus | No | 1.64 (0.88-3.09) | 0.12 |
| | Yes | 1.93 (0.86-4.31) | 0.11 |
| Smoking | No | 1.71 (0.74-3.97) | 0.21 |
| | Active | 1.78 (0.98-3.25) | 0.06 |
| LDL-/HDL-ratio | ≤3 | 1.51 (0.79-2.89) | 0.21 |
| | >3 | 2.18 (1.01-4.72) | 0.05 |
| Multi vessel disease | No | 2.73 (0.99-7.57) | 0.05 |
| | Yes | 1.58 (0.90-2.77) | 0.11 |
| C-reactive protein | ≤2.34 mg/l | 1.48 (0.55-3.97) | 0.44 |
| | >2.34 mg/l | 1.58 (0.88-2.83) | 0.13 |
| B-type natriuretic peptide | ≤37.48 pg/ml | 1.19 (0.50-2.86) | 0.70 |
| | >37.48 pg/ml | 2.41 (1.32-4.42) | 0.004 |

Median levels were used to dichotomize continous variables.
*adjusted for sex only
**adjusted for age only

TABLE 3

Hazard ratios for future cardiovascular events according to quartiles of baseline procalcitonin, C-reactive protein and B-type natriuretic peptide

| | | N | Events (%) | HR (95% CI) age-/sex-adjusted | P-value | HR (95% CI) fully adjusted* | P-value |
|---|---|---|---|---|---|---|---|
| Procalcitonin (ng/ml) | | | | | | | |
| Q1 | <0.010 | 254 | 12 (5%) | 1 | | 1 | |
| Q2 | 0.010-0.013 | 259 | 16 (6%) | 1.51 (0.71-3.19) | 0.29 | 1.58 (0.74-3.35) | 0.24 |
| Q3 | 0.014-0.020 | 301 | 17 (6%) | 1.47 (0.70-3.10) | 0.31 | 1.54 (0.73-3.26) | 0.26 |
| Q4 | >0.020 | 310 | 27 (9%) | 2.27 (1.14-4.51) | 0.02 | 2.08 (1.04-4.18) | 0.04 |
| | Per SD increment | | | 1.41 (1.07-1.86) | 0.01 | 1.33 (1.02-1.74) | 0.04 |
| C-reactive protein (mg/l) | | | | | | | |
| Q1 | <1.22 | 282 | 11 (4%) | 1 | | 1 | |
| Q2 | 1.22-2.34 | 282 | 14 (5%) | 1.27 (0.57-2.80) | 0.56 | 1.08 (0.48-2.42) | 0.86 |
| Q3 | 2.35-4.95 | 279 | 19 (7%) | 1.65 (0.78-3.47) | 0.19 | 1.33 (0.62-2.87) | 0.46 |
| Q4 | >4.95 | 281 | 28 (10%) | 2.48 (1.23-5.02) | 0.01 | 1.87 (0.89-3.92) | 0.10 |
| | Per SD increment | | | 1.42 (1.14-1.76) | 0.002 | 1.33 (1.05-1.67) | 0.02 |

TABLE 3-continued

Hazard ratios for future cardiovascular events according to quartiles of baseline procalcitonin, C-reactive protein and B-type natriuretic peptide

|    |   | N | Events (%) | HR (95% CI) age-/sex-adjusted | P-value | HR (95% CI) fully adjusted* | P-value |
|----|---|---|---|---|---|---|---|
| B-type natriuretic peptide (pg/ml) | | | | | | | |
| Q1 | <11.97 | 258 | 9 (4%) | 1 | | 1 | |
| Q2 | 11.97-37.48 | 258 | 8 (3%) | 1.04 (0.40-2.71) | 0.94 | 1.08 (0.41-2.83) | 0.88 |
| Q3 | 37.49-99.40 | 258 | 15 (6%) | 2.03 (0.87-4.71) | 0.10 | 2.11 (0.89-4.99) | 0.09 |
| Q4 | >99.40 | 258 | 32 (12%) | 5.16 (2.34-11.39) | <0.001 | 5.74 (2.51-13.11) | <0.001 |
|    | Per SD increment | | | 1.84 (1.42-2.38) | <0.001 | 1.93 (1.47-2.54) | <0.001 |

*Multivariate risk factor adjustment included age, sex, body-mass index, hypertension, diabetes, smoking status, LDL-/HDL-ratio, number of diseased vessels, statin and beta-blocker therapy.

TABLE 4

Final model of a backward multiple stepwise cox regression analysis for cardiovascular risk predictors

| Variable | Hazard ratio (95% CI) | P-value |
|---|---|---|
| Procalcitonin (1 SD increase) | 1.30 (1.00-1.70) | 0.05 |
| LDL-/HDL-ratio (1 SD increase) | 1.32 (1.03-1.70) | 0.03 |
| Sex | 0.57 (0.34-0.96) | 0.03 |
| Diabetes mellitus (IDDM) | 2.75 (1.53-4.92) | 0.001 |

TABLE 5

Final model of a backward multiple stepwise cox regression analysis for cardiovascular risk predictors

| Variable | Hazard ratio (95% CI) | P-value |
|---|---|---|
| Procalcitonin ≥0.05 ng/ml | 4.22 (2.07-8.59) | <0.001 |
| LDL-/HDL-ratio (1 SD increase) | 1.34 (1.04-1.73) | 0.03 |
| Sex | 0.60 (0.36-1.00) | 0.05 |
| Diabetes mellitus (IDDM) | 2.74 (1.54-4.87) | 0.001 |

TABLE 6

Incremental effects of procalcitonin, C-reactive protein and B-type natriuretic peptide (all log-transformed) on the area under the ROC-curve in addition to classical risk factors (basic model) for the prediction of the primary endpoint after 2 years

| Model | AUC | 95% CI |
|---|---|---|
| Basic model | 0.74 | 0.67-0.81 |
| Basic model + PCT | 0.77 | 0.70-0.84 |
| Basic model + CRP | 0.75 | 0.67-0.82 |
| Basic model + BNP | 0.79 | 0.72-0.87 |
| Basic model + PCT + CRP | 0.77 | 0.70-0.84 |
| Basic model + PCT + BNP | 0.81 | 0.74-0.88 |
| Basic model + CRP + BNP | 0.80 | 0.73-0.87 |
| Basic model + PCT + CRP + BNP | 0.81 | 0.74-0.88 |

TABLE 7

Hazard ratios and 95% confidence interval for future cardiovascular events according to baseline levels of procalcitonin and B-type natriuretic peptide in combined analysis (fully adjusted*)

| N | Procalcitonin (highest quartile >0.021 ng/ml) | B-type natriuretic peptide (highest quartile >99.40 pg/ml) | Hazard ratio 95% confidence interval | P-value |
|---|---|---|---|---|
| 654 | − | − | 1 | |
| 212 | + | − | 1.13 (0.56-2.29) | 0.74 |
| 190 | − | + | 2.44 (1.30-4.56) | 0.005 |
| 68 | + | + | 7.04 (3.40-14.57) | <0.001 |

*Multivariate risk factor adjustment included age, sex, body-mass index, hypertension, diabetes, smoking status, LDL-/HDL-ratio, number of diseased vessels, statin and beta-blocker therapy.

The invention claimed is:

1. A method for assessing the risk of future cardiovascular events in an individual with stable coronary artery disease (CAD), the method comprising:
   (a) contacting a blood, plasma, or serum sample from the individual with antibodies of a dual antibody assay for the determination of PCT with a functional assay sensitivity of <0.007 ng/ml PCT to determine the level of procalcitonin (PCT) in said plasma or serum sample from the individual; (b) determining the level of brain natriuretic protein (BNP) in said sample; and
   (c) identifying the individual as being at highest risk of experiencing future adverse cardiovascular events when the PCT level is equal to or greater than 0.05 ng/ml and the BNP level is greater than 99.4 pg/ml.

2. The method of claim 1, wherein said brain natriuretic protein (BNP) comprises BNP, proBNP and associated proBNP-fragments.

UNITED STATES PATENT AND TRADEMARK OFFICE
CERTIFICATE OF CORRECTION

PATENT NO.        : 9,217,742 B2
APPLICATION NO.   : 14/223517
DATED             : December 22, 2015
INVENTOR(S)       : Bergmann et al.

It is certified that error appears in the above-identified patent and that said Letters Patent is hereby corrected as shown below:

On the Title Page:

In the Assignee (73): Delete "B.R.A.H.M.S. GmbH" and insert -- B.R.A.H.M.S GmbH --

Signed and Sealed this
Nineteenth Day of April, 2016

Michelle K. Lee
*Director of the United States Patent and Trademark Office*